April 5, 1960

M. J. MURRAY

Plant Pat. 1,928

MINT PLANT

Filed June 10, 1959

INVENTOR.
MERRITT J. MURRAY
BY
Lindley E. Mills

United States Patent Office

Plant Pat. 1,928
Patented Apr. 5, 1960

1,928

MINT PLANT

Merritt J. Murray, Kalamazoo, Mich., assignor to A. M. Todd Company, Kalamazoo, Mich., a corporation of Michigan Application June 10, 1959, Serial No. 819,520

1 Claim. (Cl. 47—59)

Figure 1:
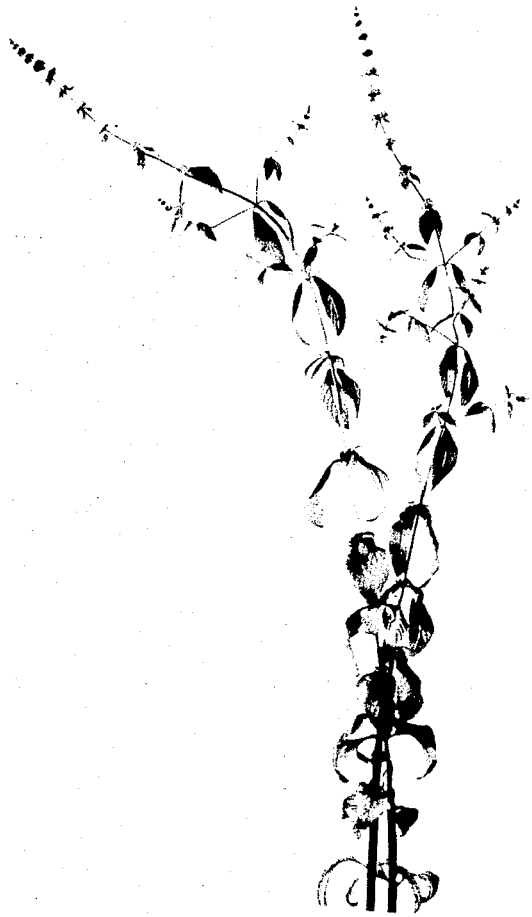

This invention relates to a new and distinct variety of mint plant which was initially produced by hybridization of tetraploid *Mentha arvensis* L. var. *piperascens* Briq. as the seed parent with a first generation hybrid of tetraploid *Mentha sylvestris* L. (*Mentha longifolia* (L.) Huds.) by *Mentha crispa* L. (*Mentha spicata* L. var. *crispata*) and thereafter asexually reproduced from stolons at nurseries near Kalamazoo, Michigan. It has also been asexually reproduced in central Washington and in north central Oregon. This hybridization was carried out using a different individual plant as the pollen parent from that used in the hybridization leading to the variety described and claimed in Plant Patent No. 1,613.

The new variety is characterized by its erect habit, by its vigor and by its hardy nature and less susceptibility to winter-killing than either *Mentha arvensis* L. var. *piperascens* Briq. or the variety of Plant Patent No. 1,613. It generally grows to a height of about three feet, or somewhat more, under central Washington field conditions. The plants are much more branched than either *Mentha arvensis* L. var. *piperascens* Briq. or the variety of Plant Patent No. 1,613. The stems are smaller than those of *Mentha arvensis* L. var. *piperascens* Briq. The new variety is characterized further by the high total menthol content of its oil.

The leaves are generally smaller than those of either *Mentha arvensis* L. var. *piperascens* Briq. or the variety of Plant Patent No. 1,613 and are often slightly less deep green in color than those of *Mentha arvensis* L. var. *piperascens* Briq. The leaves are characteristically not crisp and generally give the appearance of drooping. The leaf serrations are somewhat more numerous and even, as well as being sharper and broader at the base, than those of the leaves of *Mentha arvensis* L. var. *piperascens* Briq. The coloring of the leaf stems and veins is not distinctive. The stems and leaves are essentially non-hairy.

The flowers are borne in axillary globular clusters, the leaves on the flower spikes being bract-like and much smaller than the leaves on the non-flowering stems. These smaller leaves develop later into well-formed leaves, those adjacent to the lower flower clusters on the flower spikes often being from one-half to two-thirds normal size by the time the flowers open.

The new variety is moderately susceptible to powdery mildew, *Erysiphe cichoracearum* D.C., and to spearmint rust, frequently identified as *Puccinia menthae* Pers. It is moderately resistant to verticillium wilt, *Verticillium albo-atrum* R. & B. var. *menthae* Nelson, and is only slightly susceptible to leaf spot diseases, including *Cephalosporum sp.*, which attack *Mentha arvensis* L. var. *piperascens* Briq.

The resistance of the new variety to these organisms was demonstrated in field plots on upland and muck soils near Mentha, Michigan. Disease conditions were accentuated by interplantings of plots of *Mentha arvensis* L. var. *piperascens* Briq. and of *Mentha citrata* Ehrh., *Mentha piperita* L., *Mentha cardiaca* (Gerarde or Baker?), *Mentha spicata* L. as well as of other susceptible wild species and a number of susceptible hybrid varieties under test, including the variety of Plant Patent No. 1,613. Mildew conditions were accentuated by distributing greenhouse grown plants of *Mentha arvensis* L. *piperascens* Briq. heavily infested with powdery mildew over the plots.

Susceptible varieties, including *Mentha arvensis* L. var. *piperascens* Briq., were heavily infested with mildew and leaf spot diseases. The new variety was infested only slightly with leaf spot and to somewhat greater extent with powdery mildew, spearmint rust and Verticillium wilt. The new variety suffered considerably less winter-killing than the variety of Plant Patent No. 1,613.

Test procedures carried out near Toppenish, Washington, under conditions of ditch irrigation on leaf spot diseases and mildew gave comparable results.

The new variety is especially remarkable for the high content of total menthol in its oil as compared with the variety of Plant Patent No. 1,613. The oil of the new variety generally contains from about 79 to about 81 percent of total menthol as determined by the method for total menthol content given in the United States Pharmacopoeia No. 14.

Figure 2:
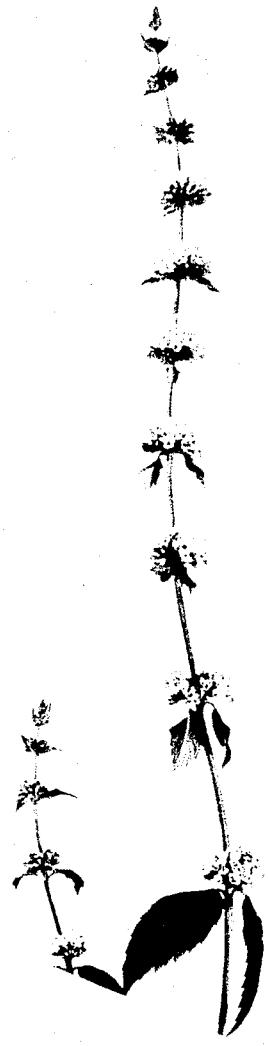

In the drawings, which are photographic illstrations of the new variety:

Figure 1 is a side view of a pair of branches of the new variety illustrating certain of its characteristics, and Figure 2 is an enlarged view of a flower stem illustrating the habit of the new variety of bearing its flowers in axillary clusters and illustrating the serrated, generally drooping nature of the leaves.

The hybridization leading to the new variety was carried out in the summer of 1952 in southern Michigan. The seed resulting from the hybridization was planted and grown in the spring and summer of 1953. The new variety was selected from among a large number of other hybrids as being of commercial value because of its hardy nature, its resistance to winter-killing and the high total menthol content of its oil. The new pariety was first asexually reproduced in the spring of 1954 in central Washington and near Kalamazoo, Michigan. It has been grown since 1954 by asexual reproduction from stolons, part of the time in central Washington and part of the time in north central Oregon. It has consistently exhibited its hardy nature, its lack of winter-kill and the high total menthol content of its oil.

I claim:

A new and distinct variety of mint plant substantially as described, characterized by its hardy nature and low susceptibility to winter-killing, by its more branching nature and drooping appearance of its leaves and by the high total menthol content of its oil, all as compared with the variety of Plant Patent No. 1,613.

No references cited.